US008968281B2

(12) United States Patent
Krishnan et al.

(10) Patent No.: US 8,968,281 B2
(45) Date of Patent: Mar. 3, 2015

(54) HANDHOLDABLE LASER DEVICE FEATURING SENSOR FOR EYE SAFE ACTIVATION

(75) Inventors: Srinivasan Krishnan, Trumbull, CT (US); Peter Simpson, West Newton, MA (US); Thomas Gerard Parent, West Newton, MA (US); Xiaomin Yan, Norwood, MA (US)

(73) Assignee: Illuminage Beauty, Ltd., Yokne'am Illit (IL)

( * ) Notice: Subject to any disclaimer, the term of this patent is extended or adjusted under 35 U.S.C. 154(b) by 0 days.

(21) Appl. No.: 13/413,747

(22) Filed: Mar. 7, 2012

(65) Prior Publication Data
US 2013/0030422 A1 Jan. 31, 2013

Related U.S. Application Data

(60) Provisional application No. 61/512,433, filed on Jul. 28, 2011.

(51) Int. Cl.
*A61B 18/20* (2006.01)
*A61N 5/06* (2006.01)
(Continued)

(52) U.S. Cl.
CPC .............. *A61N 5/0616* (2013.01); *A61B 18/203* (2013.01); *A61B 2017/00734* (2013.01);
(Continued)

(58) Field of Classification Search
CPC ........... A61B 2018/00452; A61B 2018/00476; A61B 2018/00458; A61B 18/20; A61B 18/203; A61B 2019/465; A61B 2018/202; A61B 2018/00684; A61B 2018/00875; A61N 2005/067; A61N 5/0616; A61N 2005/0633; A61N 2005/0644; A61N 2005/0659

USPC ............................................................. 606/9
See application file for complete search history.

(56) References Cited

U.S. PATENT DOCUMENTS 5,810,801 A   9/1998 Anderson et al.
7,220,254 B2 * 5/2007 Altshuler et al. ................. 606/9
(Continued)

FOREIGN PATENT DOCUMENTS

EP         2151261 A1      2/2010
WO     WO2008070747 A2    6/2008
WO    WO 2011069926 A2 *  6/2011

OTHER PUBLICATIONS

International Search Report, PCT/EP2012/063921, mailed Sep. 5, 2012, 4 pages.
(Continued)

*Primary Examiner* — Gary Jackson
*Assistant Examiner* — Boniface N Nganga
(74) *Attorney, Agent, or Firm* — Smith Risley Tempel Santos LLC; Gregory S. Smith, Esq.; Patrick D. Lowder, Esq.

(57) ABSTRACT

A laser device for treating skin is provided which includes a handholdable housing; a laser member arranged within the housing emitting an output beam; a capacitance sensor arranged at the first end of the housing which includes a plate surrounding and defining a window through which the output beam exits, the plate having at least three segments with each flexibly movable in and out of a common plane, each of the segments being connected to an electrode, the electrodes operating to determine dielectric constants of a skin surface; a signal and control storage device communicating with the sensor comparing input signals of measured dielectric constant values to a stored standard dielectric constant value, and wherein emission of the output beam is activated to fire only when all of the at least three segments align in a plane and sense the stored standard dielectric constant value.

5 Claims, 6 Drawing Sheets

(51) Int. Cl.
    *A61B 17/00*    (2006.01)
    *A61B 18/00*    (2006.01)
    *A61B 19/00*    (2006.01)
    *A61N 5/067*    (2006.01)

(52) U.S. Cl.
    CPC ........... *A61B 2018/00684* (2013.01); *A61B 2018/00875* (2013.01); *A61B 2018/202* (2013.01); *A61B 2019/465* (2013.01); *A61N 2005/0633* (2013.01); *A61N 2005/0644* (2013.01); *A61N 2005/0659* (2013.01); *A61N 2005/067* (2013.01)
    USPC .......................................................... 606/9

(56) References Cited

U.S. PATENT DOCUMENTS

| | | | |
|---|---|---|---|
| 7,856,985 | B2 | 12/2010 | Mirkov et al. |
| 7,892,525 | B2 | 2/2011 | Faivre et al. |
| 2004/0073104 | A1* | 4/2004 | Brun del Re et al. ......... 600/372 |
| 2004/0167502 | A1 | 8/2004 | Weckwerth et al. |
| 2007/0179481 | A1 | 8/2007 | Frangineas et al. |
| 2007/0185553 | A1 | 8/2007 | Kennedy |
| 2007/0198004 | A1 | 8/2007 | Altshuler et al. |
| 2007/0213696 | A1* | 9/2007 | Altshuler et al. ................ 606/9 |
| 2008/0058783 | A1 | 3/2008 | Altshuler et al. |
| 2008/0082089 | A1 | 4/2008 | Jones et al. |
| 2008/0262482 | A1 | 10/2008 | Hantash et al. |
| 2008/0294152 | A1 | 11/2008 | Altshuler et al. |
| 2009/0043294 | A1* | 2/2009 | Island et al. ..................... 606/9 |
| 2010/0069898 | A1 | 3/2010 | O'Neil et al. |
| 2010/0082020 | A1* | 4/2010 | Gong et al. .................... 606/12 |
| 2011/0040358 | A1 | 2/2011 | Bean et al. |
| 2011/0098789 | A1* | 4/2011 | Weckwerth et al. ............ 607/88 |

OTHER PUBLICATIONS

Co-Pending U.S. Appl. No. 13/413,740, filed Mar. 7, 2012; titled "Handholdable Laser Device Featuring Flexible Connection Between a Laser and a Printed Circuit Board".

Co-Pending U.S. Appl. No. 13/419,674, filed Mar. 14, 2012; titled Handholdable Laser Device Featuring Pulsing of a Continuous Wave Laser.

* cited by examiner

HANDHOLDABLE LASER DEVICE FEATURING SENSOR FOR EYE SAFE ACTIVATION

BACKGROUND OF THE INVENTION

1. Field of the Invention

The invention concerns a cordless handholdable laser device featuring a sensor controlling beam activation to insure an eye safe operation.

2. The Related Art

Devices based on light amplification by stimulated emission of radiation (laser) have revolutionized many areas of dermatological medicine and of cosmetics. Amongst skin conditions responsive to treatment are acne scars, rosacea, hyperpigmentation, unwanted hair and dermal rejuvenation. Ablative resurfacing has become a common method for cosmetic rejuvenation. Wrinkle reduction has been a particular objective of the phototherapy.

Advances in laser based devices and their use in skin treatment methods have been many during the last decade. Several publications have focused on safe arming of the device to avoid unintended exposures. U.S. 2004/0167502 A1 (Weckwerth et al.) reports optical sensors for detecting engagement with a skin surface. The sensors are based upon multiple light emitting diodes, each having a unique wavelength band, and a broad-band photodetector to measure the remission of light at multiple wavelengths from a material being analyzed. U.S. 2010/0082020 (Gong et al.) describes a medical laser having a capacitance sensor and an emission control device to insure that a laser handpiece is in contact with skin prior to activation. The handpiece needs to stand perpendicular to the skin surface before any surgical operation begins.

Most electromagnetic radiation delivery devices for treatment of skin are relatively large pieces of equipment. Complexity in their basic engineering and mode of operation defeats miniaturization into a handheld device. For instance, U.S. 2008/0082089 A1 (Jones et al.) describes a system including a first solid-state and a second solid-state laser. A respective first output beam is fed into the second device for generating excitation in a rare earth doped gain medium to produce a second output beam. The latter is used to treat skin. U.S. 2007/0179481 A1 (Frangineas et al.) seeks to treat skin laxity with a plurality of pulses from a carbon dioxide laser. The system requires a housing to contain a scanning apparatus and a tip connected to a vacuum pump for exhausting smoke resulting from ablation.

Many of the reported ablative procedures require special cooling mechanisms. For instance, U.S. Pat. No. 5,810,801 directs a beam of radiation to penetrate the dermal region below a wrinkle to injure collagen. A cooling system is then activated to prevent injury of the overlying epidermis. These cooling systems are often quite bulky.

Another problem with the state of the art, particularly with portable instruments, is in their effectiveness to emit sufficiently energetic doses of electromagnetic radiation. U.S. 2011/0040358 A1 (Bean et al.) provides one solution describing a portable device which is eye safe operating between 1350-1600 nm to treat wounds and diseases. This is a battery operated system that need not directly contact tissue. A key part of the device is a lens constructed to have the laser beam converge to a focal point slightly above the tissue surface target.

SUMMARY OF THE INVENTION

A laser device for treating skin is provided which includes:
(i) a handholdable housing with a first end and a second end;
(ii) a laser member arranged within the housing and emitting an output beam;
(iii) a capacitance sensor arranged at the first end of the housing including a plate surrounding and defining a window through which the output beam exits, the plate having at least three segments each flexibly movable in and out of a common plane, each of the segments being connected to an electrode, the electrodes operating to determine dielectric constant of a skin surface; and
(iv) a signal and control storage device communicating with the sensor comparing input signals of measured dielectric constant values to a stored standard dielectric constant value;

wherein emission of the output beam is activated to fire only when all of the at least three segments align in a plane and sense the stored standard dielectric constant value.

BRIEF DESCRIPTION OF THE DRAWING

Further features, aspects and benefits of the present invention will become more readily apparent from consideration of the following drawing in which.

DETAILED DESCRIPTION OF THE INVENTION

Now we have developed a laser device in a highly compact handholdable configuration for treating skin. In a preferred format, the device is cordless and meets power needs through a rechargeable battery.

Safety, especially with respect to eye damage, has been addressed by a special capacitance sensor. The sensor in a preferred embodiment is an annular ring of three sections, each connected to a different electrode. The laser member will not fire until all segments of the annular ring are firmly placed against the skin and are all registering a dielectric constant appropriate to a skin surface.

Figure 1:
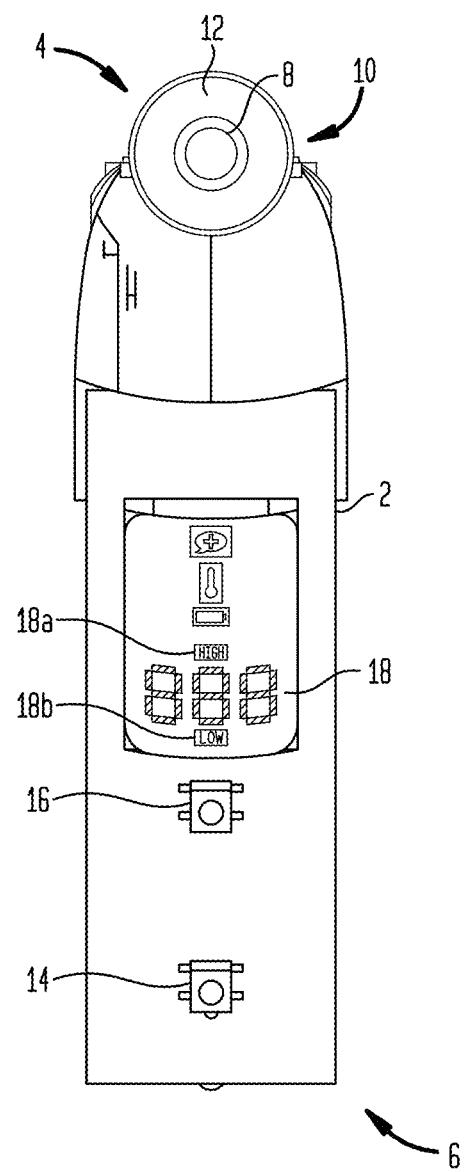
FIG. 1 is a front view of one embodiment of the invention.
Figure 2:
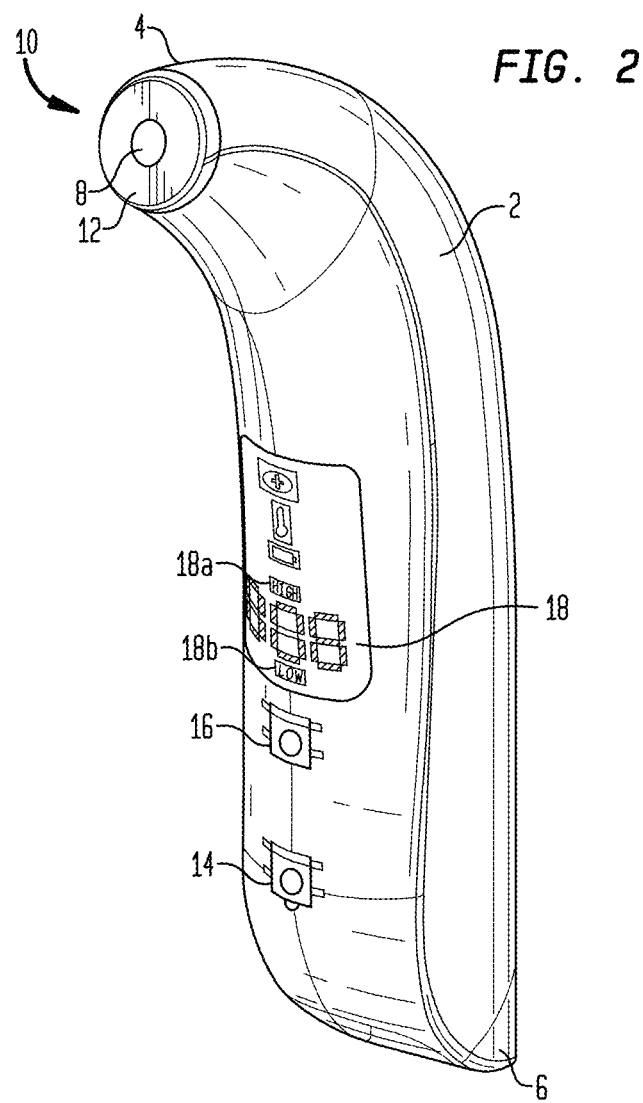
FIG. 2 is a plan perspective view of the embodiment according to FIG. 1.

FIGS. 1 and 2 reveal a first embodiment of this invention. The laser device features a curvilinear housing 2 having a first end 4 and an opposite second end 6. An aperture defining a window 8 is formed at a tip 10 of the first end of the housing.

The housing preferably has a sinusoidal or S-shape. This allows the tip 10 to be properly oriented against a user's face and simultaneously permits viewing by the user of power settings and activation. A longitudinal axis along a length of the housing and an axis traversing through the window at a point of intersection will define an angle between 100° and 170°, preferably between 110° and 160°, and optimally between 120° and 140°.

Figure 3:
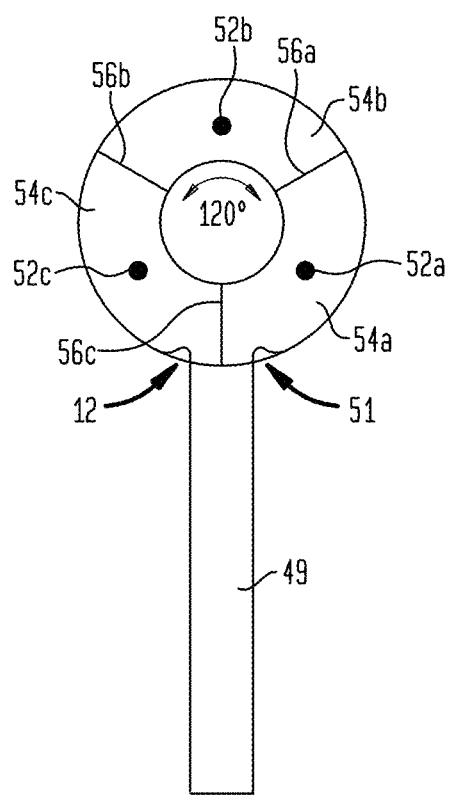
FIG. 3 is a front view focused on the sensor and connecting electrodes.
Figure 4:
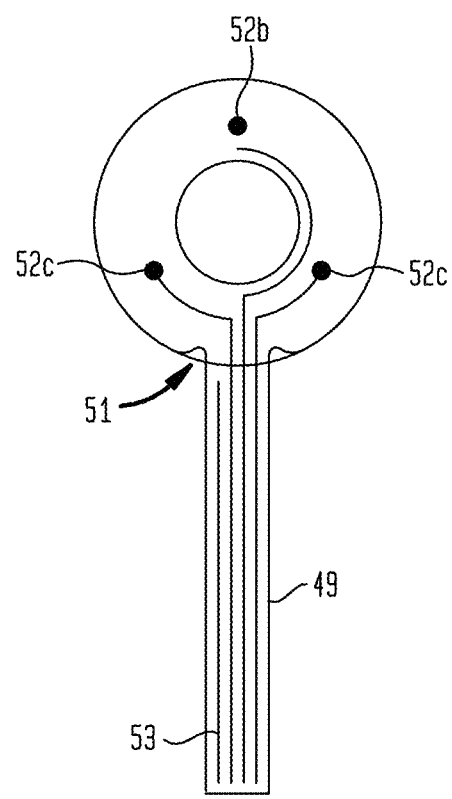
FIG. 4 is a rear view of the sensor with electrodes shown in FIG. 3.

The capacitance sensor 50 as best shown in FIGS. 3 and 4 is the form of an annular plate 12 and arranged at the first end of the housing. The annular plate surrounds window 8. The plate is opaque to electromagnetic radiation. Any output beam of electromagnetic radiation is emitted through the window 8 which is an open central area of the annular plate. A bend relief joint 51 at a right angle connects the plate to an elongate arm 49 that electrically communicates with a printed circuitboard 28.

The annular plate has at least three segments 54a, 54b, 54c each flexibly and independently movable in and out of a common plane. Each of the segments is connected to an electrode 52a, 52b, 52c. Dummy contact wires 53 serve as reference. Between each of the segments is a gap 56a, 56b, 56c of 1 to 20 mil.

By arranging the electrodes in a ring, they stay concentric to the cross section of the window 8 through which the electromagnetic radiation is emitted. The arrangement maximizes the surface area of the sensor and allows maintenance of the smallest possible volume around the window 8.

The capacitive sensor includes two conductors with a capacitance field between them. There are three capacitive switches related to each of the three electrodes. Each of the switches must satisfy a condition that it has the capacitance correlated with proper dry skin contact. When there is only partial contact with the skin, the dielectric is improper and firing of the laser member cannot occur.

Two control buttons are activatable from outside the housing. One is a power activating button 14 functioning to arm/power on the device. The other is a power setting button 16 functioning to control the power level. The term "button" is to be interpreted broadly. Although in the first embodiment, the buttons are square, these may in other embodiments be of a round or other geometrical shape. Also these buttons may be movable inward/outward from a surface of the housing, but in another embodiment may be a non-movable touch screen form of switch.

In conjunction with the power setting button, there is a light emitting diode (LED) 18 for indicating the setting of high or low power 18a and 18b.

Figure 5:
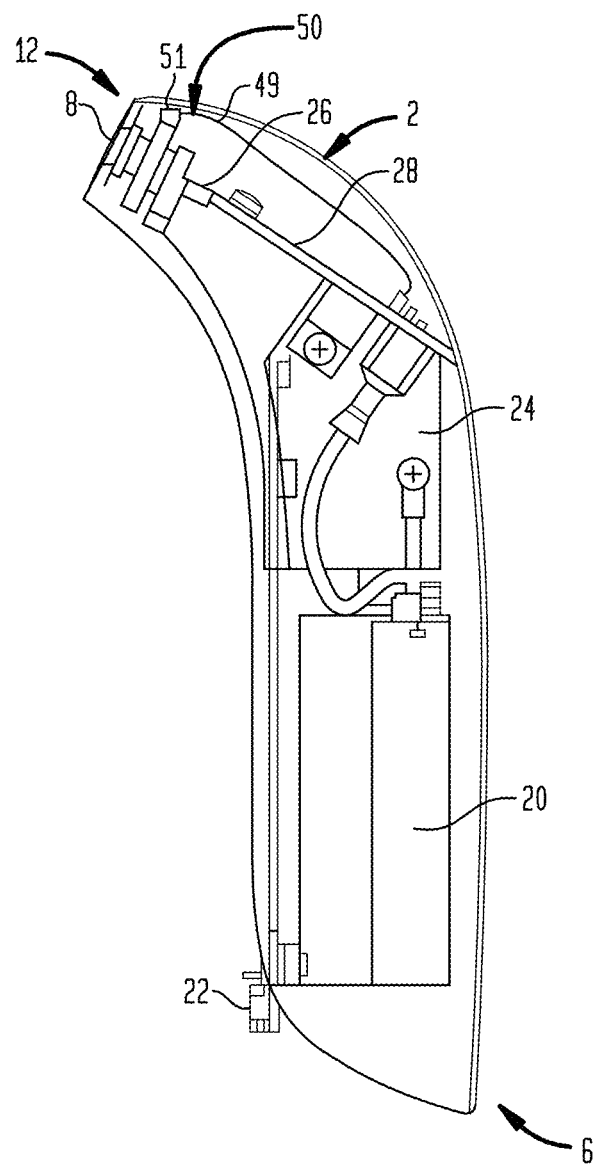
FIG. 5 is a cross-sectional view of FIG. 1 taken perpendicular to that view.
Figure 6:
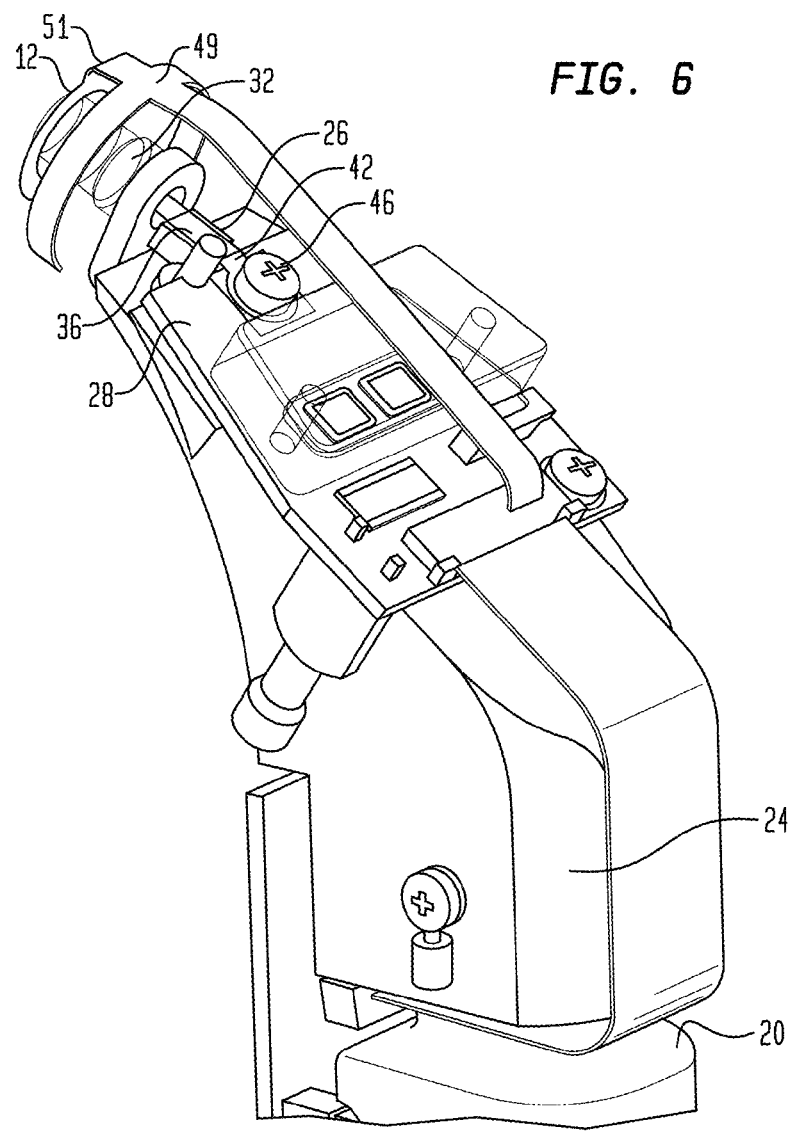
FIG. 6 is a view of the internal mechanism separated from the housing of FIG. 1.
Figure 7:
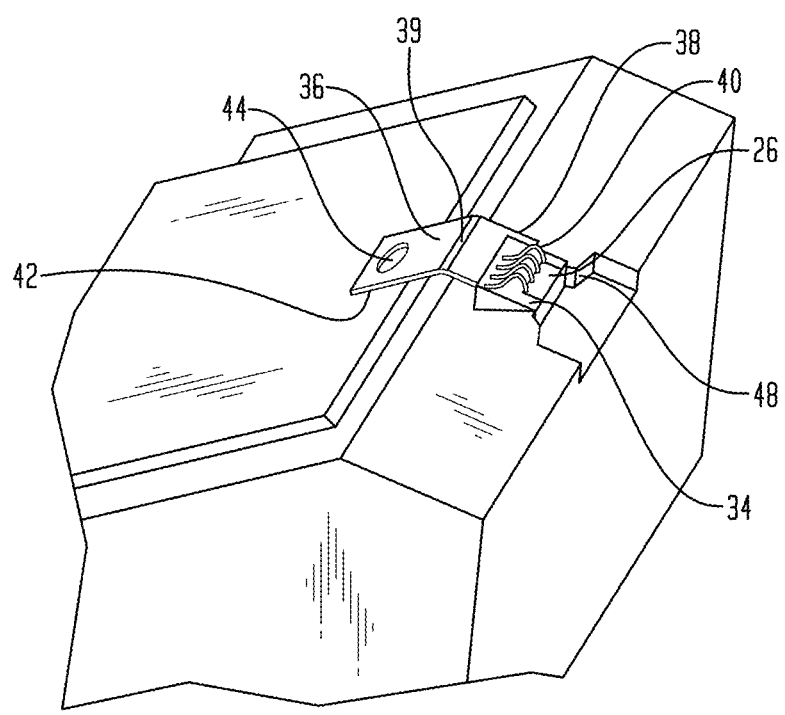
FIG. 7 is a semi-schematic view of a portion of FIG. 6 encompassing the laser member and the signal and control storage device.

FIGS. 5 and 6 reveal the inner mechanism of the laser device. A rechargeable battery 20 is lodged within a lower area of the housing just above the rear end 6. Recharging is achieved by connection of an outside power source to port 22 electrically communicating with the rechargeable battery.

Above the battery is an aluminum block 24 serving both as a support and solid coolant to dissipate heat generated by the laser member. The device neither needs nor features any special liquid or gas coolant system.

A laser member 26 generating electromagnetic radiation is supported on an arm of the aluminum block. The laser member of this embodiment operates on a constant output power delivering a continuous wave over time. It is a solid state diode laser including the elements indium, arsenic, gallium and tin. The laser produces a pulse of radiation having a wavelength between approximately 1300 and 1600 nm, preferably between 1420 and 1470 nm, and optimally about 1440 nm. Fluence may range between 0.5 and 5 joules/cm$^2$, more preferably between 1 and 3 joules/cm$^2$, and optimally between 1.3 and 1.8 joules/cm$^2$. Electromagnetic radiation emanating from the laser device is non-ablative to the skin being classified by the U.S. Food & Drug Administration as a Class I/1 inherently safe rating.

Upstream from the laser member 26 is a signal and control storage device in a form of a printed circuitboard 28 supported on the arm of the aluminum block 24. Operation of the device is controlled by the printed circuitboard including power switching, radiation fire sequencing, generation, timing, sequencing of laser pulses and processing of skin contact information. With regard to the latter, the signal and control storage device communicates with the sensor comparing input signals of measured dielectric constant values to a stored standard dielectric constant value of skin. Emission of the output beam is activated to fire only when all of the at least three segments align in a plane and sense the stored standard dielectric constant value.

Between the laser member 26 and the aluminum block 24 is a submount 34 as best seen in FIG. 5. The submount directly supports the laser member and also a flexible electrically conductive connector 36 carrying signals/current from the printed circuitboard 28. The flexible electrically conductive connector features forward and rear ends 38, 42. An area 39 between the forward and rear ends is highly bendable. The bending may range from 0 to 360° in angle. This allows various angles between a major plane of the laser member and a major plane of the printed circuitboard. Preferably, the angle is held between 10 and 250°. This flexibility in orientation creates a geometric and ergonomic advantage.

The forward end of the flexible connector is bonded to the submount. A portion of the forward end features a set of several wire bonds 40 which complete the electrical connection to the laser member 26. The rear end 42 of the flexible connector features an aperture 44 for a screw 46 or other fastening member to achieve a press contact with the printed circuitboard. The screw and a washer assembly provides an evenly distributed force which compresses a large area of the flexible connector to a plated contact on the printed circuit board. This arrangement minimizes contact resistance, thus lowering electrical power loss. This arrangement also allows for ease of assembly, disassembly and replacement.

The flexibility of the connector allows the system to escape the ordinarily required connection of circuitry to be in a plane of the output beam generated by the laser. Flexible connectors in one embodiment of this invention are formed of a set of copper wires sandwiched between layers of polyimide.

Fashioned in a downstream area of the submount 34 is an alignment structure 48 with outwardly tapering walls. The alignment structure receives the forward end 38 of the flexible connector to prevent movement and insuring the laser member is properly oriented.

In summary, the present invention is described above in terms of a preferred and other embodiments. The invention is not limited, however, to the described and depicted embodiments. Rather, the invention is only limited by the claims appended hereto.

What is claimed is:

1. A laser device for treating skin comprising:
   a handholdable housing with a first end and a second end;
   a laser member arranged within the housing and emitting an output beam;
   a capacitance sensor arranged at the first end of the housing comprising a plate formed as an annular ring surrounding and defining a window through which the output beam exits, the plate having at least three segments having a gap of 1-20 mil therebetween, with each segment being flexibly and independently movable in and out of a common plane, each of the segments being connected to an electrode, the electrodes operating to determine dielectric constant of a skin surface; and
   a signal and control storage device communicating with the sensor comparing input signals of measured dielectric constant values to a stored standard dielectric constant value; wherein the signal and control storage device is a printed circuitboard;

wherein emission of the output beam is activated to fire only when all of the at least three segments align in a plane and sense the stored standard dielectric constant value; and wherein the gap of the plate comprises a non-electrical conductive material.

2. The device according to claim 1 wherein the output beam emits electromagnetic radiation of wavelength ranging from 1420 to 1470 nm.

3. The device according to claim 1 wherein the output beam has a fluence range from 0.5 to 5 joules/cm$^2$.

4. The device according to claim 1 wherein the output beam has a fluence range from 1 to 3 joules/cm$^2$.

5. The device according to claim 1, wherein the laser device also comprises a solid coolant operative to dissipate heat generated by the laser member obviating the need for a liquid or gas coolant system.

* * * * *